United States Patent [19]

Koda et al.

[11] 4,311,842

[45] Jan. 19, 1982

[54] CEPHALOSPORIN COMPOUNDS

[75] Inventors: Akio Koda; Ichiro Isaka, both of Hoya; Yukiyasu Murakami, Urawa, all of Japan

[73] Assignee: Yamanouchi Pharmaceutical Co., Ltd., Tokyo, Japan

[21] Appl. No.: 53,852

[22] Filed: Jul. 2, 1979

[30] Foreign Application Priority Data

Jul. 20, 1978 [JP] Japan .................................. 53-88994

[51] Int. Cl.³ .......................................... C07D 501/56
[52] U.S. Cl. ...................................... 544/27; 544/21; 544/28
[58] Field of Search ............................. 544/28, 27, 21

[56] References Cited

U.S. PATENT DOCUMENTS 4,098,888 7/1978 Ochiai et al. ........................... 544/27
4,110,327 8/1978 Saikawa et al. ....................... 544/28
4,165,373 8/1979 Yamada et al. ....................... 544/28
4,217,348 8/1980 Treuner et al. ....................... 544/28

Primary Examiner—Paul M. Coughlan, Jr.
Attorney, Agent, or Firm—Burgess, Ryan and Wayne

[57] ABSTRACT

Cephalosporin compounds shown by the general formula

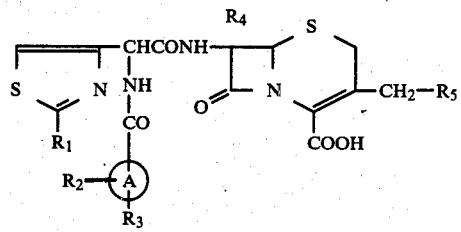

wherein $R_1$ represents hydrogen atom or an amino group; $R_2$ and $R_3$, which may be the same or different, each represents hydrogen atom, a hydroxy group, an oxo group, a lower alkyl group, or a lower alkoxy group; $R_4$ represents a hydrogen atom or a lower alkoxy group; $R_5$ represents an acetoxy group or $—S—R_6$ (wherein $R_6$ represents a 5- or 6-membered nitrogen-containing heterocyclic group which can be substituted by a lower alkyl group or lower alkoxy group); and A represents a monocyclic or bicyclic heterocyclic ring containing one or two atoms selected from the group consisting of nitrogen, oxygen and a sulfur atom; and pharmaceutically acceptable nontoxic salts thereof.

These compounds have excellent antimicrobial activity against various microorganisms including resistant bacteria and are used for the treatment of bacterial infections of animals including human beings.

8 Claims, No Drawings

CEPHALOSPORIN COMPOUNDS

DETAILED DESCRIPTION OF THE INVENTION

This invention relates to the novel cephalosporin compounds shown by the following general formula and the pharmaceutically acceptable nontoxic salts thereof;

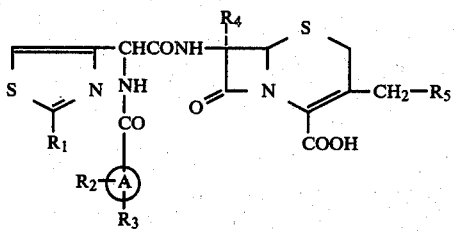

wherein $R_1$ represents a hydrogen atom or an amino group; $R_2$ and $R_3$, which may be the same or different, each represents hydrogen atom, a hydroxy group, an oxo group, a lower alkyl group, or a lower alkoxy group; $R_4$ represents a hydrogen atom or a lower alkoxy group; $R_5$ represents an acetoxy group or —S—$R_6$ (wherein $R_6$ represents a 5- or 6-membered nitrogen-containing heterocyclic group which can be substituted by a lower alkyl group or lower alkoxy group); and A represents a monocyclic or bicyclic heterocyclic ring containing one or two atoms selected from the group consisting of nitrogen, oxygen and a sulfur atom.

The invention also relates to a process of producing the cephalosporin compounds shown by the above-mentioned general formula I and the pharmaceutically acceptable nontoxic salts thereof.

The compounds of this invention have excellent antimicrobial activity against various microorganisms including resistant bacteria and are useful for the treatment of infectious diseases of animals including human beings.

In the field of antibiotics, a great number of antibiotic compounds have been synthesized and a number of those compounds have already been practically used. The generalized application of antibiotics to various bacterial infections resulted in a new problem of the acquisition of resistance in bacteria. For overcoming this problem, further investigations for new antiobiotics have been demanded and proceeded. Furthermore, the diversified pathogenic bacteria of infectious diseases have given rise to the development or discovery of new antibiotics having the characteristic that they are effective not only against specific pathogenic bacteria but also do not act against other bacteria, or cause new resistance in other bacteria.

As such antibiotics, sodium 7β-[2-aminothiazol-4-yl)glycinamido]-3-(1-methyl-1H-tetrazol-5-ylthiomethyl)-3-cephem-4-carboxylate, etc., are disclosed in U.S. Pat. No. 4,098,888 (corresponding patents in other countries are West German Offenlegungsschriften Nos. 2,556,736 and 2,559,942; French Pat. Nos. 2,294,690 and 2,357,552)

As the result of further investigation for compounds having more unique antimicrobial activity, the inventors have succeeded in discovering the novel and most useful compounds of this invention.

That is, the invention provides the novel cephalosporin compounds shown by general formula I described above and the pharmaceutically acceptable nontoxic salts thereof.

In general formula I, the lower alkyl group includes, for example, a methyl group, ethyl group, isopropyl group, butyl group, hexyl group, etc., and the lower alkoxy group includes, for example, methoxy group, ethoxy group, isopropoxy group, butoxy group, hexyloxy group, etc. In the formula, A represents a monocyclic or bicyclic heterocyclic ring including one or two atoms selected from the group consisting of nitrogen, oxygen and a sulfur atom as described above and as such heterocyclic rings, there are 6-membered heterocyclic rings such as pyridine, pyrimidine, pyran, thiopyran, etc., and a heterocyclic ring formed by two condensed 6-membered rings, such as quinoline, isoquinoline, naphthylidine, etc. Also, as the 5- or 6-membered nitrogen-containing heterocyclic ring shown by $R_6$, there are, for example, thiazole, isothiazole, thiadiazole, oxadiazole, triazole, tetrazole, pyrimidine, pyridazine, pyrazine, etc.

The pharmaceutically acceptable nontoxic salts of the compounds of general formula I are, for example, the alkali metal salts such as sodium salts, potassium salts, etc.; the ammonium salts; and the organic base salts such as cyclohexylamine salts, dicyclohexylamine salts, trimethylamine salts, triethylamine salts, ethanolamine salts, ornithine salts, lysine salts, etc.

The compounds of general formula I and their salts of them are all novel compounds; they have excellent antibacterial activity against gram positive bacteria and gram negative bacteria, in particular, against the latter, and are useful as medicaments.

Typical examples of the cephalosporin compounds shown by general formula I are as follows:

7-[2-(4-Hydroxy-6-methylnicotinamido)-2-(thiazol-4-yl)acetamido]cephalosporanic acid, 7-(4-oxo-4H-thiopyran-3-carboxamido)-2-(thiazol-4-yl)acetamido]-3-(1-methyltetrazol-5-yl)thiomethyl-Δ³-cephem-4-carboxylic acid, 7-[2-(2-aminothiazol-4-yl)-2-(4-hydroxy-6-methylnicotinamido)acetamido]-3-(1-methyltetrazol-5-yl)thiomethyl-Δ³-cephem-4-carboxylic acid, 7-[2-(2-aminothiazol-4-yl)-2-(4-oxo-4H-thiopyran-3-carboxamido)acetamido]cephalosporanic acid, 7-[2-(4-hydroxy-6-methylnicotinamido)-2-(thiazol-4-yl)acetamido]-3-(1-methyltetrazol-5-yl)thiomethyl-Δ³-cephem-4-carboxylic acid, 7-[2-(4-hydroxy-6-methylnicotinamido)-2-(2-aminothiazol-4-yl)acetamido]cephalosporanic acid, 7-[2-(4-oxo-4H-thiopyran-3-carboxamido)-2-(thiazol-4-yl)acetamido]cephlosporanic acid, 7-[2-(2-aminothiazol-4-yl)-2-(4-oxo-4H-thiopyran-3-carboxamido)acetamido]-3-(1-methyltetrazol-5-yl)thiomethyl-Δ³-cephem-4-carboxylic acid, 7β-[2-(2-aminothiazol-4-yl)-2-(4-hydroxy-6-methylnicotinamido)acetamido]-7α-methoxy-3-(1-methyltetrazol-5-yl)thiomethyl-Δ³-cephem-4-carboxylic acid, 7β-[2-(2-aminothiazol-4-yl)-2-(4-oxo-4H-thiopyran-3-carboxamido)acetamido]-7α-methoxy-3-(1-methyltetrazol-5-yl)thiomethyl-Δ³-cephem-4-carboxylic acid, 7-[2-(4-hydroxy-6-methoxynicotinamido)-2-(thiazol-4-yl)acetamido]cephalosporanic acid, 7β-[2-(4-hydroxy-6-methylnicotinamido)-2-(thiazol-4-yl)acetamido]-7α-methoxycephalosporanic acid, 7-[2-(isoquinoline-3-carboxamido)-2-(thiazol-4-yl)acetamido]-cephalosporanic acid, 7-[2-(4-hydroxy-6-methoxynicotinamido)-2-(thiazol-4-yl)acetamido]-3-(1-methyltetrazol-5-yl)thiomethyl-Δ³-cephem-4-carboxylic acid, 7β-[2-(4-hydroxy-6-methylnicotinamido)-2-(thiazol-4-yl)acetamido]-7α-methoxy-3-(1-methyltetrazol-5-yl)thiomethyl-Δ³-cephem-4-carboxylic acid, and 7-[2-(isoquinoline-3-carboxamido)-2-(thiazol-4-yl)acetamido]-3-(1-methyltetrazol-5-yl)thiomethyl-Δ³-cephem-4-carboxylic acid.

The cephalosporin compounds represented by general formula I are prepared by reacting a compound shown by general formula II

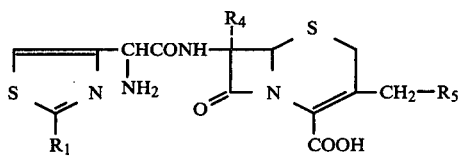

wherein $R_1$, $R_4$ and $R_5$ have the same significance as in general formula I and a compound of the general formula III

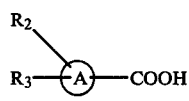

wherein $R_2$, $R_3$ and A have the same significance as in general formula I or the reactive derivatives thereof.

It is preferred to perform the reaction by reacting a compound of formula II and an equimolar amount or excessive molar amount of a compound of formula III in a solvent, under cooling or at room temperature in the presence of, preferably, a base.

The solvent used in this case may be an organic solvent which does not affect the reaction, such as methanol, ethanol, acetone, chloroform, methylene chloride, ethylene chloride, tetrahydrofuran, acetonitrile, ethyl acetate, ethyl formate, dimethylformamide, etc., and mixtures of them. Also, as the base used in the above reaction, suitably these are organic bases, alkali carbonates, alkali hydrogencarbonates, etc., but tertiary amines such as triethylamine, pyridine, dimethylaniline, etc., are preferably used.

The compounds of formula I thus prepared may be isolated and purified by conventional procedures.

Preferred examples of the reactive compounds shown by formula III are the acid halides, mixed acid anhydrides, active esters, active amides, acid anhydrides, acid azides, etc.

When a compound of formula III is reacted in the free form, it is preferred to use a condensing agent such as N,N'-dicyclohexylcarbodiimide, N,N'-diethylcarbodiimide, etc.

Furthermore, the cephalosporin compounds of formula I wherein $R_5$ is an acetoxy group can be converted into a compound shown by general formula I' included in general formula I

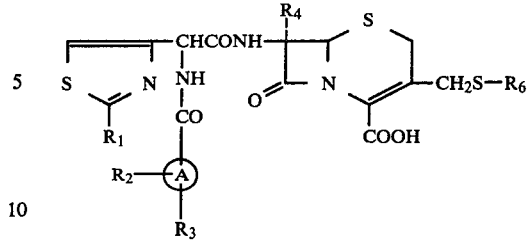

wherein $R_1$, $R_2$, $R_3$, $R_4$, $R_6$ and A have the same significance as in general formula I by reacting with a thiol compound shown by general formula IV $$HS{-}R_6 \qquad \text{IV}$$

wherein $R_6$ has the same significance as in general formula I or an alkali metal salt thereof.

This reaction is performed usually in a solvent at room temperature or under heating. The solvent used in the reaction is an organic solvent which does not take part in the reaction, such as acetone, dimethylformamide, methanol, ethanol, etc., as well as water, a phosphate buffer, or a mixture of them. It is preferred to perform a reaction at about neutral conditions. When the compound of formula IV is used in the free form, it is preferred to perform the reaction in the presence of a base such as an alkali hydroxide, an alkali carbonate, an alkali hydrogencarbonate, trialkylamine, pyridine, dimethylaniline, etc.

The compounds of formula I can be also prepared by reacting a compound shown by general formula V

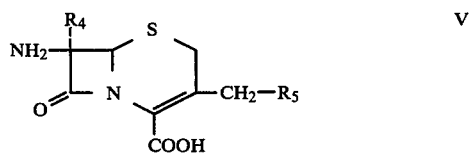

wherein $R_4$ and $R_5$ have the same significance as in general formula I and a compound shown by the general formula VI

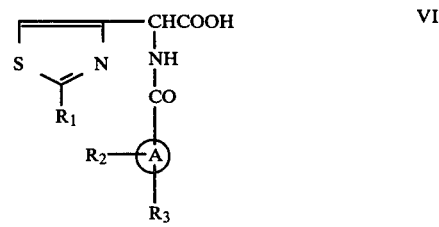

wherein $R_1$, $R_2$, $R_3$ and A have the same significance as in general formula I or a reactive derivative thereof.

The reaction conditions are substantially the same as those in a reaction of the compound of formula II and a compound of formula III described above.

After the reaction is over, the reaction mixture is acidified and the product thus precipitated is recovered by filtration or the product is recovered from the reaction mixture by extraction with a suitable solvent. The compounds of formula I thus obtained can be converted to the pharmaceutically acceptable nontoxic salts thereof by a conventional manner. For example, the alkali metal salt of a compound of formula I is obtained by adding a n-butanol solution of an alkali 2-ethylhexanoate to a compound of formula I and further adding an organic solvent having a different solubility, such as ether, ethyl acetate, etc., to the mixture. The organic base salt of a compound of formula I is obtained by adding an equivalent or a slightly excessive amount of an organic base such as dicyclohexylamine, triethylamine, cyclohexylamine, trimethylamine, etc., to a compound of formula I. Also, the ammonium salt of a compound of formula I is obtained by adding aqueous ammonia to the compound.

The compounds of formula I or the pharmaceutically acceptable nontoxic salts thereof are administered orally or parenterally as an antibacterial agent. The doses of the medicament depend upon the symptoms, weight, etc., of patients but are usually 250–3,000 mg/day per adult, and the medicament is administered 3-4 times a day.

The forms of the medicament of this invention suitable for administration are injections, tablets, capsules, syrups, etc., and the medicament is formed by adding conventional excipients, preservatives, stabilizers, etc.

The antibacterial activity (the minimum inhibitory concentration) of the compounds of this invention shown by formula I is shown in the following table in comparison to those of known compounds having similar structures, 7-[2-amino-2-(2-aminothiazol-4-yl)acetamido]-3-(1-methyl-tetrazol-5-yl)thiomethyl-$\Delta^3$-cephem-4-carboxylic acid (Compound A) having the following formula

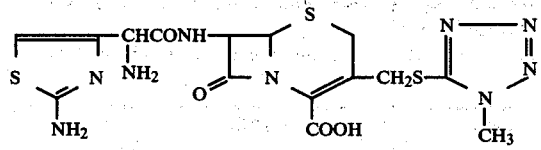

and 7-[2-amino-2-(2-aminothiazol-4-yl)acetamido]cephalosporanic acid Compound B) having the following formula;

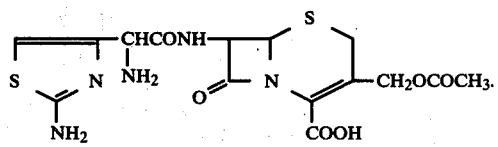

EXAMPLE 1

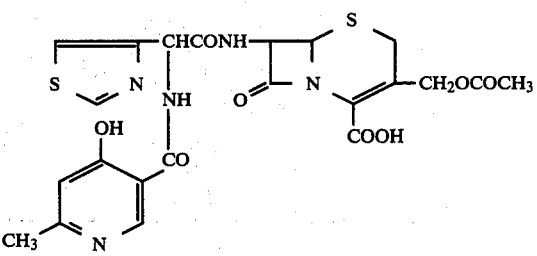

In 15 ml of methanol was suspended 1.03 g of 7-[2-amino-2-(thiazol-4-yl)acetamido]cephalosporanic acid and after cooling the suspension to $-5°$ C., 0.7 ml of triethylamine and then 15 ml of methylene chloride were added to the suspension. To the mixture was added 850 mg of 4-hydroxy-6-methylnicotinic acid N-hydroxysuccinimide ester pyridine adduct and the resulting mixture was stirred for 4 hours at $-5°$ C. to $5°$ C. The solvent was distilled off from the reaction mixture under reduced pressure and after adding 10 ml of water and then 10 ml of ethyl acetate to the residue, the mixture was adjusted to pH 2 with 6 N hydrochloric acid. The crystalline powder formed was recovered by filtration, washed with water and then ethyl acetate, and dried over phosphorus pentoxide under reduced pressure to provide 850 mg of DL-7-[2-(4-hydroxy-6-methylnicotinamido)-2-(thiazol-4-yl)acetamido]-cephalosporanic acid.

Nuclear magnetic resonance spectra (DMSO-$d_6$):

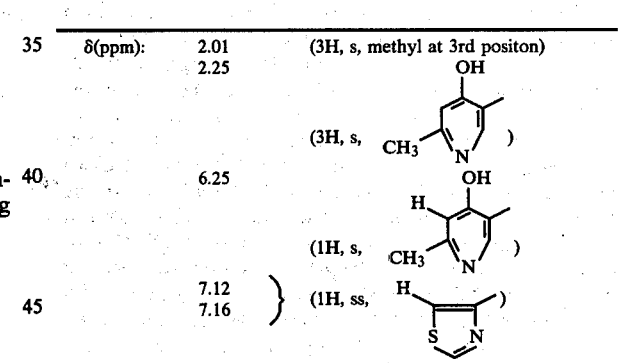

| Compound Bacteria | minimum inhibitory concentration (γ/ml) | | | | | | | | | |
|---|---|---|---|---|---|---|---|---|---|---|
| | Example No. | | | | | | | | Compound | |
| | 1 | 2 | 3 | 4 | 5 | 6 | 7 | 8 | A | B |
| *Bacillus subtilis* ATCC 6633 | 3.13 | 6.25 | 3.13 | 1.56 | 3.13 | 1.56 | 3.13 | 3.13 | 12.5 | 1.56 |
| *Staphylococcus aureus* ATCC 6538P | 3.13 | 6.25 | 3.13 | 1.56 | 1.56 | 1.56 | 1.56 | 1.56 | 25 | 3.13 |
| *Staphylococcus aureus* Oonuma (penicillin, Streptomycin-resistant) | 6.25 | 12.5 | 6.25 | 6.25 | 6.25 | 3.13 | 6.25 | 6.25 | 100 | 12.5 |
| *Staphylococcus aureus* 209P | 1.56 | 3.13 | 1.56 | 1.56 | 0.78 | 0.78 | 1.56 | 1.56 | 12.5 | 3.13 |
| *Corynebacterium xerosis* | 3.13 | 6.25 | 3.13 | 1.56 | 3.13 | 1.56 | 6.25 | 3.13 | 25 | 3.13 |
| *Vibrio* Hy 133 | 0.78 | 0.78 | 0.78 | 0.78 | 0.39 | 0.78 | 0.78 | 0.78 | 6.25 | 1.56 |
| *Proteus vulgaris* OXK US | 1.56 | 0.78 | 1.56 | 3.13 | 1.56 | 0.19 | 0.19 | 1.56 | 6.25 | 3.13 |
| *Pseudomonas aeruginosa* NCTC 10490 | 1.56 | 1.56 | 25 | 6.25 | 1.56 | 0.78 | 0.39 | 0.78 | 100 | >100 |
| *Salmonella enteritidis* 1891 | 3.13 | 0.78 | 0.39 | 6.25 | 0.78 | 0.19 | 0.09 | 0.78 | 0.78 | 0.78 |
| *Proteus mirabilis* IFM OM-9 | 3.13 | 0.39 | 0.78 | 6.25 | 1.56 | 0.09 | 0.09 | 1.56 | 1.56 | 1.56 |
| *Pseudomonas aeruginosa* ATCC 8689 | 25 | 50 | 100 | 100 | 50 | 50 | 25 | 25 | >100 | >100 |
| *Pseudomonas aeruginosa* 99 (Gentamicin-resistant) | 25 | 25 | 100 | 100 | 50 | 50 | 12.5 | 12.5 | >100 | >100 |

| | |
|---|---|
| 8.28 | (1H, s, 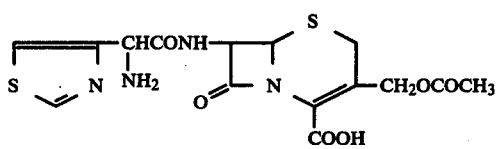) |
| 8.44 | (1H, s, ) |

Infrared spectra ($\nu_{max}^{KBr}$ cm$^{-1}$) 3350, 2950, 1770, 1735, 1660, 1520.

Production of the starting material:

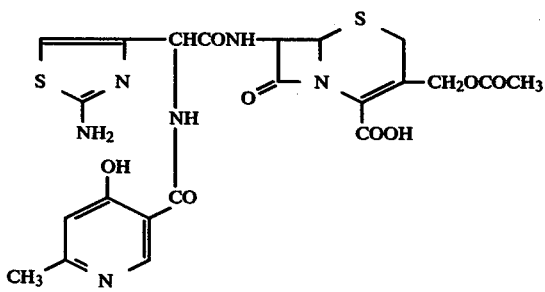

In a mixture of 30 ml of N,N-dimethylformamide and 40 ml of methylene chloride was dissolved 5.16 g of 2-tert-butoxy-carbonylamido-2-(thiazol-4-yl)acetic acid and after adding 8.0 g of 7-aminocephalosporanic acid benzhydryl ester and then 3.76 g of N,N'-dicyclohexyl-carbodiimide to the solution, the resultant mixture was stirred for 2.5 hours at room temperature. Methylene chloride was distilled off from the reaction mixture under reduced pressure and 300 ml of water and then 300 ml of ethyl acetate were added to the residue.

The organic layer was separated and washed with an aqueous 5% sodium hydrogencarbonate solution and then water, and dried over anhydrous magnesium sulfate. After distilling off the solvent under reduced pressure, the residue obtained was treated with 6 ml of anisole and 50 ml of trifluoroacetic acid for one hour at room temperature and then added to 250 ml of ether to provide 7.95 g of the trifluoroacetic acid salt of the desired product. The product was dissolved in 40 ml of methanol and after adjusting the solution to pH 5 with triethylamine, 40 ml of isopropyl alcohol was added thereto. The powder thus formed was recovered by filtration, washed with isopropyl alcohol, and dried over phosphorus pentoxide in vacuo to provide 5.0 g of 2-amino-2-(thiazol-4-yl)acetamido-cephalosporanic acid.

EXAMPLE 2

By following the same procedure as in Example 1 using 1.07 g of 2-amino-2-(2-aminothiazol-4-yl)acetamidocephalosporanic acid and 850 mg of 4-hydroxy-6-methylnicotinic acid N-hydroxysuccinimide ester pyridine adduct, 850 mg of DL-7-[2-(4-hydroxy-6-methylnicotinamido)-2-(2-aminothiazol-4-yl)acetamido]cephalosporanic acid was obtained.

EXAMPLE 3

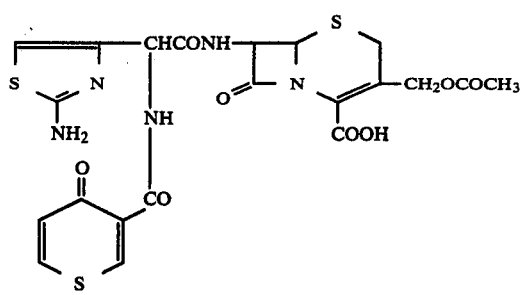

In a mixture of 15 ml of methanol and 15 ml of methylene chloride was suspended 1.07 g of 7-[2-amino-2-(2-aminothiazol-4-yl)acetamido]cephalosporanic acid. To the suspension was added 0.9 ml of triethylamine with stirring. To the resulting solution was added 460 mg of 4-oxo-4H-thiopyran-3-carbonyl chloride at −15° C. and the mixture was stirred for 3 hours at the same temperature. The solvent was distilled off from the reaction mixture under reduced pressure and after adding 60 ml of cold water and then 50 ml of ethyl acetate to the residue, the mixture was adjusted to pH 3.5 with 6 N hydrochloric acid. The crystalline powder formed was recovered by filtration and washed with water to provide 800 mg of DL-7-[2-(2-aminothiazol-4-yl)-2-(4-oxo-4H-thiopyran-3-carboxamido)-acetamido]cephalosporanic acid.

Nuclear magnetic resonance spectra (DMSO-d$_6$):

| δ(ppm): | | |
|---|---|---|
| 2.01 | (—OCOCH$_3$) | |
| 7.20 | (d, J = 10Hz, | ) |
| 8.36 | (dd, J = 4, 10Hz, | ) |
| 9.30 | (d, J = 4Hz, | ) |

EXAMPLE 4

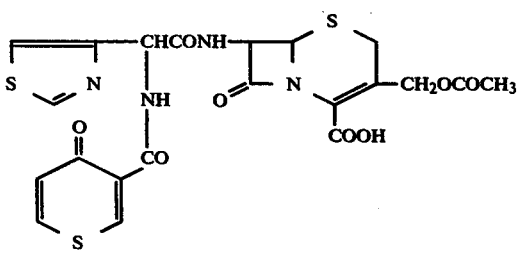

By following the same procedure as in Example 3 using 1.03 g of 7-[2-amino-2-(thiazol-4-yl)acetamido]-cephalosporanic acid and 450 mg of 4-oxo-4H-thiopyran-3-carbonyl chloride, 700 mg of DL-7-[2-(4-oxo-4H-thiopyran-3-carboxamido)-2-(thiazol-4-yl)acetamido]-cephalosporanic acid was obtained.

EXAMPLE 5

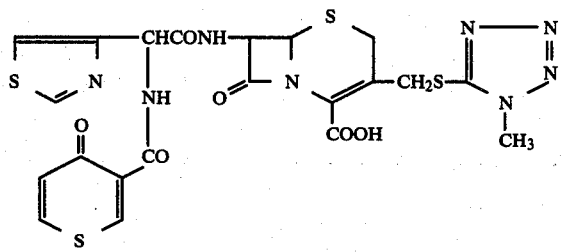

In a mixture of 15 ml of methanol and 15 ml of methylene chloride was suspended 1.14 g of 7-[2-amino-2-(thiazol-4-yl)acetamido]-3-(1-methyltetrazol-5-yl)thiomethyl-$\Delta^3$-cephem-4-carboxylic acid. To the suspension was added 0.7 ml of triethylamine with stirring. To the resulting solution was added 650 mg of 4-oxo-4H-thiopyran-3-carboxylic acid N-hydroxysuccinimide ester at 0° C. and the reaction mixture was stirred for 4 hours at the same temperature. After the same treatment of the reaction mixture, as in Example 1, 1.14 g of DL-7-[2-(4-oxo-4H-thiopyran-3-carboxamido)-2 -(thiazol-4-yl)acetamido]-3-(1-methyltetrazol-5-yl)thiomethyl-$\Delta^3$-cephem-4-carboxylic acid was obtained.

Nuclear magnetic resonance spectra (DMSO-$d_6$):

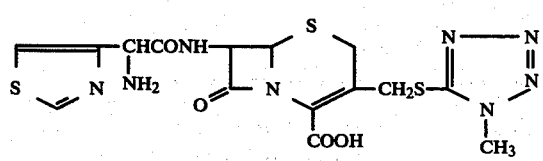

Production of the starting material:

By following the same procedure as the case of producing the raw material in Example 1 using 2.68 g of 2-tert-butoxycarbonylamino-2-(thiazol-4-yl)acetic acid and 4.94 g of 7-amino-3-(1-methyltetrazol-5-yl)thiomethyl-$\Delta^3$-cephem-4-carboxylic acid benzhydryl ester, condensing them with N,N'-dicyclohexylcarbodiimide, removing the both protective groups using trifluoroacetic acid and 5 ml of anisole, and neutralizing with the amine, 2.7 g of 7-[2-amino-2-(thiazol-4-yl)acetamido]-3-(1-methyltetrazol-5-yl)thiomethyl-$\Delta^3$-cephem-4-carboxylic acid was obtained.

EXAMPLE 6

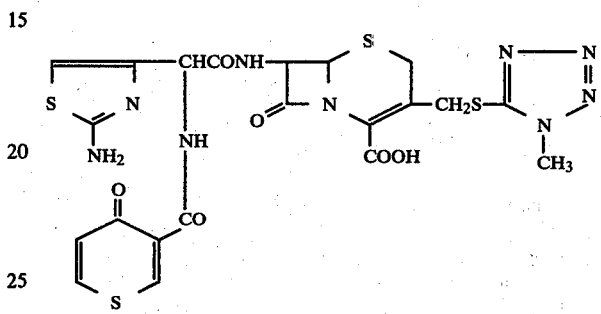

By following the same procedure as in Example 5 using 1.18 g of 7-[2-amino-2-(2-aminothiazol-4-yl)acetamido]-3-(1-methyltetrazol-5-yl)thiomethyl-$\Delta^3$-cephem-4-carboxylic acid and 650 mg of 4-oxo-4H-thiopyran-3-carboxylic acid succinimide ester, there was obtained 1.10 g of DL-7-[2-(2-aminothiazol-4-yl)-2-(4-oxo-4H-thiopyran-3-carboxyamido)acetamido]-3-(1-methyltetrazol-5-yl)thiomethyl-$\Delta^3$-cephem-4-carboxylic acid.

EXAMPLE 7

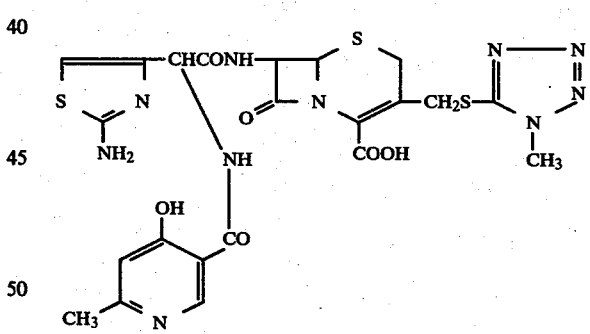

In a mixture of 15 ml of methanol and 15 ml of methylene chloride was suspended 1.18 g of 7-[2-amino-2-(2-aminothiazol-4-yl)acetamido]-3-(1-methyltetrazol-5-yl)thiomethyl-$\Delta^3$-cephem-4-carboxylic acid and 0.7 ml of triethylamine and the mixture was stirred. To the resulting solution was added 850 mg of 4-hydroxy-6-methylnicotinic acid N-hydroxysuccinimide ester pyridine adduct at 0° C. and the reaction mixture was stirred for 5 hours at the same temperature.

After the same treatment of the reaction mixture as in Example 1, 1.05 g of DL-7-[2-(2-aminothiazol-4-yl)-2-(4-hydroxy-6-methylnicotinamido)acetamido]-3-(1-methyltetrazol-5-yl)thiomethyl-$\Delta^3$-cephem-4-carboxylic acid was obtained.

Nuclear magnetic resonance spectra (DMSO-$d_6$):

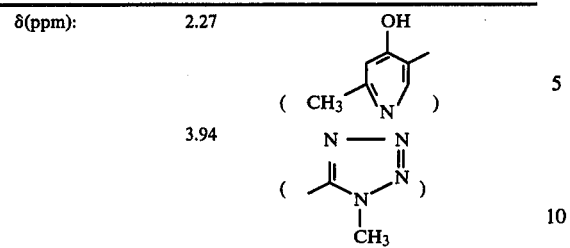

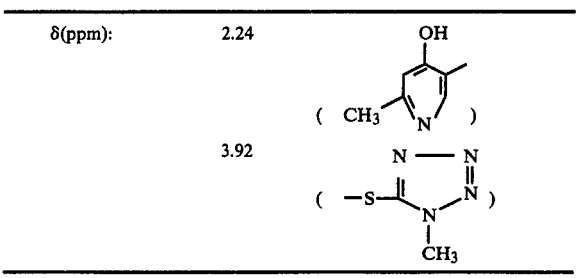

Production of the starting material:

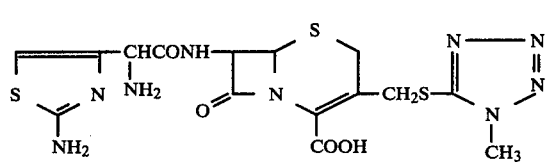

In a mixture of 20 ml of N,N-dimethylformamide and 100 ml of methylene chloride was dissolved 2.87 g of 2-(tert-butoxy-carbonylamido)-2-(2-aminothiazol-4-yl)acetic acid and 4.94 g of 7-amino-3-(1-methyltetrazol-5-yl)-thiomethyl-Δ³-cephem-4-carboxylic acid benzhydryl ester and then 2.06 g of N,N'-dicyclohexylcarbodiimide. The reaction mixture was stirred for 6 hours at room temperature. After filtering off the N,N'-dicyclohexylurea which had precipitated, the methylene chloride was distilled off from the reaction mixture under reduced pressure and then 200 ml of water and 150 ml of ethyl acetate were added to the residue thus obtained. The organic layer was separated, washed with water, and dried over anhydrous magnesium sulfate. The solvent was distilled off under reduced pressure and the residue thus obtained, was treated with 50 ml of trifluoroacetic acid and 5 ml of anisole and then neutralized with triethylamine to obtain 3.08 g of 7-[2-amino-2-(2-aminothiazol-4-yl)acetamido]-3-(1-methyltetrazol-5-yl)thiomethyl-Δ³-cephem-4-carboxylic acid.

EXAMPLE 8

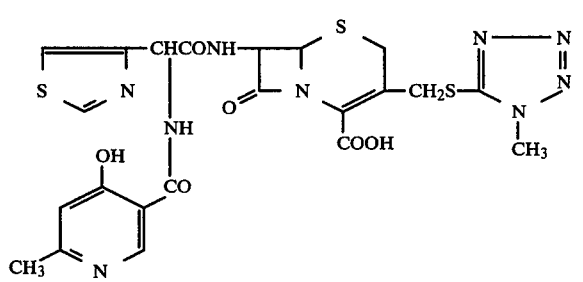

In 30 ml of water were dissolved 1.1 g of 7-[2-(4-hydroxy-6-methylnicotinamido)-2-(thiazol-4-yl)]acetamido-cephalosporanic acid and 3.4 of sodium hydrogencarbonate. To the solution was added 232 mg of 5-mercapto-1-methyltetrazole and the mixture was stirred for 8 hours at 60° C. After the reaction mixture was cooled, the solution was adjusted to pH 2 with 6 N hydrochloric acid and the crystalline powder formed was recovered by filtration and washed with water to provide 1.11 g of DL-7-[2-(4-hydroxy-6-methylnicotinamido)-2-(thiazol-4-yl)-acetamido]-3-(1-methyltetrazol-5-yl)thiomethyl-Δ³-cephem-4-carboxylic acid.

Nuclear magnetic resonance spectra (DMSO-d₆):

EXAMPLE 9

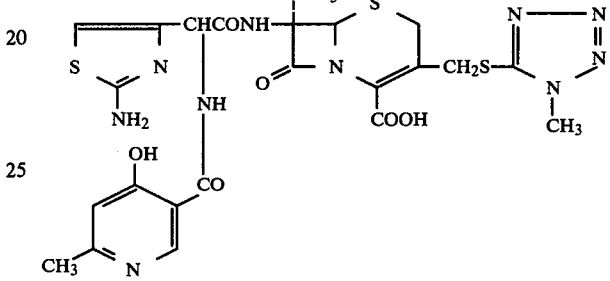

In a mixture of 5 ml of methanol and 5 ml of methylene chloride was suspended 257 mg of 7β-DL-[2-amino-2-(2-aminothiazol-4-yl)acetamido]-7α-methoxy-3-(1-methyltetrazol-5-yl)thiomethyl-Δ³-cephem-4-carboxylic acid and then 0.14 ml of triethylamine was added to the suspension. To the resulting solution at 0° C. was added 170 mg of 4-hydroxy-6-methylnicotinic acid N-hydroxysuccinimide ester pyridine adduct and the reaction mixture was stirred for 5 hours at the same temperature. After the same treatment of the reaction mixture as in Example 1, 105 mg of 7β-DL-[2-(2-aminothiazol-4-yl)-2-(4-hydroxy-6-methylnicotinamido)acetamido]-7α-methoxy-3-(1-methyltetrazol-5-yl)thiomethyl-Δ³-cephem-4-carboxylic acid was obtained.

Nuclear magnetic resonance spectra (DMSO-d₆):

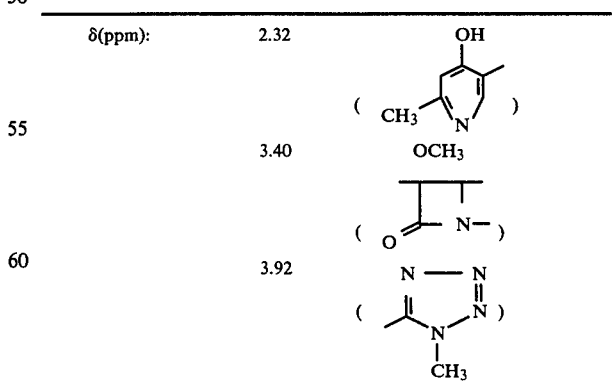

Infrared spectra $V_{max}^{KBr}$ cm⁻¹) 1760, 1660, 1620

Production of the starting material:

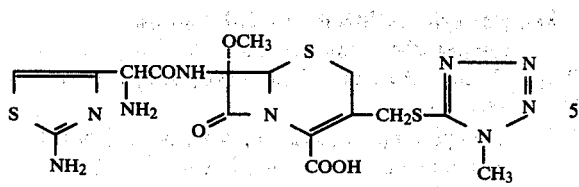

In 18 ml of 80% formic acid was dissolved 1.8 g of 7β-[2-methoxyimino-2-(2-aminothiazol-4-yl)acetamido]-7α-methoxy-3-(1-methyltetrazol-5-yl)thiomethyl-Δ³-cephem-4-carboxylic acid (anti isomer) and then 2.7 g of zinc dust was added to the solution cooled with a water-bath. After 20 minutes, insoluble materials were filtered off and the solvent was distilled off from the filtrate at temperature below room a temperature. Water was added to the residue and the mixture was neutralized with sodium hydrogencarbonate to provide 7β-DL-[2-amino-2-(2-aminothiazol-4-yl)acetamido]-7α-methoxy-3-(1-methyltetrazol-5-yl)thiomethyl-Δ³-cephem-4-carboxylic acid.

Nuclear magnetic resonance spectra (DMSO-d₆):

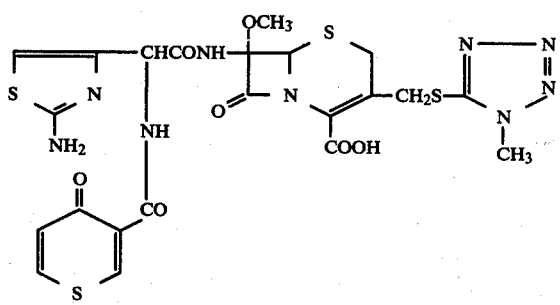

Infrared spectra $cv_{max}^{KBr}$ cm$^{-1}$) 1760, 1600~1680

EXAMPLE 10

By following the same procedure as in Example 9 using 7β-DL-[2-amino-2-(2-aminothiazol-4-yl)acetamido]-7α-methoxy-3-(1-methyltetrazol-5-yl)thiomethyl-Δ³ -cephem-4-carboxylic acid and 4-oxo-4H-thiopyran-3-carboxylic acid N-hydroxysuccinimide ester, 7β-DL-[2-(2-aminothiazol-4-yl)-2-(4-oxo-4H-thiopyran-3-carboxamido)acetamido]-7α-methoxy-3-(1-methyltetrazol-5-yl)thiomethyl-Δ³-cephem-4-carboxylic acid was obtained.

Nuclear magnetic resonance spectra (DMSO-d₆):

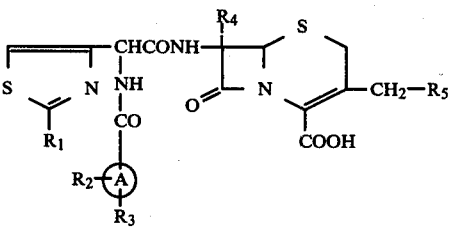

Infrared spectra ($v_{max}^{KBr}$ cm$^{-1}$) 1765, 1670, 1620

EXAMPLE 11

| Product of Example 7 | 250 g |
|---|---|
| Corn starch | 50 g |
| Talc | 5 g |
| Silicic anhydride | 1.5 g |

The above mixture was finely pulverized and filled in 1,000 capsules.

What is claimed is:

1. A cephalosporin compound represented by the general formula wherein R₁ represents a hydrogen atom or an amino group; R₂ and R₃, which may be the same or different, each represents a hydrogen atom, a hydroxy group, an oxo group, a lower alkyl group, or a lower alkoxy group; R₄ represents a hydrogen atom or a lower alkoxy group; R₅ represents —S—R₆ wherein R₆ represents a 5- or 6-membered nitrogen-containing heterocyclic group which is substitutable by a lower alkyl group or lower alkoxy group; and A represents pyridyl group or a thiopyranyl group and a pharmaceutically acceptable nontoxic salt thereof.

2. A cephalosporin compound as claimed in claim 1 wherein R₆ of general formula I is a tetrazolyl group which is substituted by a lower alkyl group.

3. A cephalosporin compound as claimed in claim 1 wherein A of general formula I is a pyridyl group.

4. A cephalosporin compound as claimed in claim 1 wherein A of general formula I is a thiopyranyl group.

5. A cephalosporin compound as claimed in claim 1 wherein $R_1$ of general formula I is an amino group.

6. A cephalosporin compound as claimed in claim 1 wherein said compound is 7-[2-(2-aminothiazol-4-yl)-2-(4-oxo-4H-thiopyran-3-carboxamido)acetamido]-3-(1-methyltetrazol-5-yl)thiomethyl-$\Delta^3$-cephem-4-carboxylic acid or a pharmaceutically acceptable nontoxic acid thereof.

7. A cephalosporin compound as claimed in claim 1 wherein said compound is 7-[2-(2-aminothiazol-4-yl)-2-(4-hydroxy-6-methylnicotinamido)acetamido]-3-(1-methyltetrazol-5-yl)thiomethyl-$\Delta^3$-cephem-4-carboxylic acid or a pharmaceutically acceptable nontoxic acid thereof.

8. A cephalosporin compound as claimed in claim 1 wherein said compound is 7-[2-(4-hydroxy-6-methylnicotinamido)-2-(thiazol-4-yl)acetamido]-3-(1-methyltetrazol-5-yl)thiomethyl-$\Delta^3$-cephem-4-carboxylic acid.

* * * * *